United States Patent [19]

Cahen et al.

[11] Patent Number: 4,781,906
[45] Date of Patent: Nov. 1, 1988

[54] CRYSTALLINE SILICAS

[75] Inventors: Raymond M. Cahen, Brussels; Guy L. G. Debras, Belgrade; Georges E. M. J. DeClippeleir, Sint Pieters Leeuw, all of Belgium

[73] Assignee: Labofina, S.A., Brussels, Belgium

[21] Appl. No.: 562,651

[22] Filed: Dec. 19, 1983

[51] Int. Cl.$^4$ .............................................. C01B 33/26
[52] U.S. Cl. .................................. 423/328; 502/232; 502/77
[58] Field of Search ............................. 423/328–332, 423/335; 502/60, 77, 232

[56] References Cited

U.S. PATENT DOCUMENTS 3,702,886 11/1972 Argauer et al. ..................... 423/328
4,061,724 12/1977 Grose et al. ......................... 423/335

OTHER PUBLICATIONS

Wu et al., "Journal of Physical Chemistry", vol. 83, No. 21, 1979, pp. 2777–2781.

*Primary Examiner*—John Doll
*Assistant Examiner*—P. Bruce Breneman
*Attorney, Agent, or Firm*—William D. Jackson; John K. Abokhair; M. Norwood Cheairs

[57] ABSTRACT

A novel crystalline silica composition having a silica to alumina atomic ratio not lower than 80 and having a certain specific X-ray diffraction pattern after calcination in air for at least 3 hours at a temperature of at least 500° C.

5 Claims, No Drawings

CRYSTALLINE SILICAS

TECHNICAL FIELD

The present invention relates to novel crystalline silicas. More particularly, the present invention is concerned with crystalline silicas which exhibit absorption and catalytic properties, typically in the field of alkylation and isomerization.

BACKGROUND OF THE ART

During the last ten years, many efforts have been made to find new types of catalysts, either in the zeolitic field, or in the crystalline silica field.

One problem with zeolite catalysts, however, is that they are subject to rapid deactivation in the presence of even small amounts of water. Rapid deactivation means that a high rate of conversion of reactants to products cannot be maintained over a long period of time thus requiring expensive catalyst changeouts or regeneration procedures which greatly reduce the efficiency of the overall process.

There is, therefore, a need for a catalyst displaying a high steam stability together with an excellent catalytic activity in alkylation reactions and particularly in para alkylation reactions.

SUMMARY OF THE INVENTION

It is therefore an object of the invention to provide new crystalline silica polymorphs of the silicalite type.

Another object of the invention is to provide new crystalline silicas having excellent catalytic activity when employed in para alkylation reactions.

Another object of the invention is to provide new crystalline silicas having not only excellent catalytic activity but exhibiting excellent steam stability.

Still another object of the invention is to provide new crystalline silicas which can be used as a molecular sieve absorbant.

A further object of the present invention is to provide new crystalline silicas which can be used in isomerization reactions.

The crystalline silicas according to the present invention are characterized as a class of compounds having a silica to alumina atomic ratio of at least 80 and in that they have the following X-ray diffraction pattern shown in Table 1 after calcination in air for at least 3 hours at a temperature of at least 500° C.

One of the most important features of the X-ray diffraction pattern of the crystalline silicas of the invention is constituted by the splitting of the peak at the interplanar spacing of $d = 3.65 \pm 0.02$ Å.

Other features of the X-ray diffraction pattern which may be used to distinguish the crystalline silicas of the invention from others, may be exemplified by the appearance at the interplanar spacing of about $d = 3.05$ to $3.06$ Å while a singlet peak appears at the interplanar spacing of about $d = 3.00 \pm 0.02$ Å.

The crystalline silicas of the invention may be prepared in accordance with a process which comprises the calcination of as-synthesized crystalline silicas at a temperature of at least 500° C. during a period of time of at least about 3 hours and in the presence of air.

DETAILED DESCRIPTION OF THE INVENTION

The crystalline silicas according to the invention are defined with reference to the X-ray powder diffraction pattern (Co-Kα radiation) which the crystalline silicas display after calcination in air for at least 3 hours at a temperature of at least 500° C. This X-ray powder diffraction pattern should contain the diffraction maxima mentioned in Table 1. The X-ray powder diffraction pattern of a typical example of a crystalline silica according to the invention is represented in Table 1. This X-ray powder diffraction pattern is typical for crystalline silica having a monoclinic symmetry.

TABLE 1

| Interplanar spacing d (Angstroms) | Relative intensity |
|---|---|
| 11.33 | 100 |
| 10.18 | 52 |
| 9.29 | 22 |
| 6.76 | 10 |
| 6.41 | 16 |
| 6.05 | 20 |
| 5.74 | 11 |
| 5.61 | 14 |
| 5.17 | 3 |
| 5.06 | 7 |
| 5.01 | 8 |
| 4.64 | 7 |
| 4.38 | 9 |
| 4.28 | 11 |
| 4.10 | 5 |
| 4.03 | 1 |
| 3.87 | 82 |
| 3.83 | 42 |
| 3.77 | 22 |
| 3.73 | 48 |
| 3.67 | 15 |
| 3.64 | 15 |
| 3.61 | 4 |
| 3.50 | 5 |
| 3.46 | 7 |
| 3.41 | 4 |
| 3.37 | 7 |
| 3.33 | 7 |
| 3.32 | 11 |
| 3.27 | 5 |
| 3.15 | 3 |
| 3.06 | 6 |
| 3.05 | 6 |
| 3.00 | 15 |
| 2.95 | 7 |
| 2.74 | 4 |
| 2.69 | 3 |
| 2.60 | 3 |
| 2.52 | 4 |
| 2.49 | 5 |
| 2.42 | 4 |
| 2.02 | 10 |
| 2.00 | 9 |
| 1.88 | 3 |

The crystalline silicas according to the invention may be prepared by hydrothermal crystallization of a reaction mixture containing water, a source of silica, an alkali metal oxide and a quaternary ammonium salt having the formula (I)

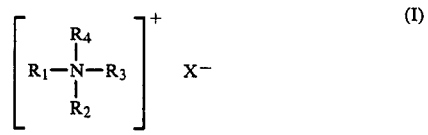

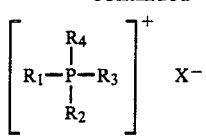

or a quaternary phosphonium salt having the formula (II), wherein $R_1$, $R_2$, $R_3$ and $R_4$ are alkyl radicals, and X is OH or the ion of a monovalent acid, at a pH between about 7 and 14, to form a hydrous crystalline precursor.

The source of silica in the reaction mixture is generally selected from alkali metal silicate, fume silica, silica sols and silica gel.

It has been noticed that these silica sources always contain minor amounts of alumina.

According to the present invention, the amount of alumina which may be present in the crystalline silicate should be so that the silica-alumina atomic ratio is not lower than 80. Preferably, silica-alumina atomic ratios should be higher than 120 while ratios higher than 200 and even 2000 may also be found.

In case of very high silica-alumina atomic ratios, the silica source to be used may be obtained by preparing a gel by controlled hydrolysis of tetraethylsilicate.

The other compound which is to be considered in the preparation of the crystalline silica is the quaternary ammonium salt, which is generally selected from the group comprising tetrapropylammonium bromide or hydroxide, and tetraethylammonium bromide or hydroxide, the tetrapropylammonium bromide being preferred.

Accordingly, in preparing the crystalline silicas, there is formed a reaction mixture having a pH of at least 10 which contains from 150 to 700 moles $H_2O$, 13 to 50 moles silica and from 0.1 to 6.5 moles $M_2O$ where M is an alkali metal, per mole-ion of the quaternary cation. The reaction mixture is maintained at a temperature from about 100° to 250° C. under autogeneous pressure until crystals of the silica are formed, ordinarily after about 50 to 150 hours. The obtained product is washed with water and dried in air at about 110° C.

The crystalline silica of the present invention is obtained by calcining the hereabove product. According to an embodiment of the present invention, the hereabove obtained crystalline silica is calcined during a period of at least 3 hours and at a temperature of at least 500° C., which preferably ranges between about 550° and about 650° C.

The following examples are given to better illustrate the method for preparing the cystalline silicas of the present invention and its properties in alkylation reactions, but without limiting its scope.

EXAMPLE 1

A crystalline silica catalyst was prepred by mixing 103 grams of colloidal silica containing 0.8% $Na_2O$ in 250 grams water with 24.3 grams of $(C_3H_7)_4N^+Br^-$ in 62 grams $H_2O$; 9.1 grams NaOH in 62 grams $H_2O$ were added to the mixture. During the synthesis the pH of the mixture has varied from 12.7 to 11.7. Afterwards the mixture was heated at 175° C. in an autoclave for 3 days. The resulting crystalline silica has the following molecular formula expressed in terms of oxide:

1 $(TPA)_2O$; 39 $SiO_2$; 3.1 $Na_2O$; 550 $H_2O$

The crystalline silica had a silica/alumina atomic ratio of 450. This crystalline silica was then calcined in the presence of air for about 10 hours at 600° C. The calcined crystalline silica had an X-ray diffraction pattern which presents a doublet at the interplanar spacing d=3.65 Å. In addition, the X-ray pattern presents a doublet at about d=3.05 to 3.06 Å and a singlet at about d=2.98 to 3.00 Å.

EXAMPLE 2

The crystalline silica prepared in Example 1 was used to carry out the alkylation of toluene by ethylene in the presence of steam at the following operating conditions.

Toluene/ethylene mole ratio: 8.1
Water/toluene mole ratio: 0.2
Inlet temperature: 410° C.
Pressure: 15 kg/cm²
Toluene WHSV: 187.5

At a 55% ethylene conversion, ethyltoluene has been obtained with a para/meta isomer ratio of 7.4.

EXAMPLE 3

A crystalline silica catalyst was prepared by mixing 370.4 grams of colloidal silica containing 0.12% $Na_2O$ in 250 grams water with 38 grams of $(C_3H_7)_4N^+Br^-$ in 200 grams $H_2O$; 15.7 grams of NaOH in 200 grams $H_2O$ were added to the mixture. During the synthesis the pH of the mixture was varied from 13.1 to 12. Afterwards the mixture was heated at 175° C. in an autoclave for 3 days. The resulting crystalline silica had the following molecular formula expressed in terms of oxide.

1 $(TPA)_2O$; 40 $SiO_2$; 3.25 $Na_2O$; 552 $H_2O$

The crystalline silica had a silica/alumina atomic ratio of 130. This crystalline silica was then calcined in the presence of air for 3 hours at 600° C. The calcined crystalline silica had an X-ray diffraction pattern which presents a doublet at the interplanar spacing d=3.65 Å.

This crystalline silica was used in an alkylation reaction as described in Example 2.

At 70% ethylene conversion, ethyltoluene was obtained with a para/meta isomer ratio of 4.8.

What we claim is:

1. Crystalline silicas characterized in that they have a silica to alumina atomic ratio of at least 80 and an X-ray diffraction pattern as set forth in Table 1, after calcination in air for at least 3 hours at a temperature of at least about 500° C.

2. Crystalline silicas according to claim 1 characterized in that they have a silica to alumina atomic ratio of at least about 120.

3. Crystalline silicas according to claim 2 characterized in that they have a silica to alumina atomic ratio of at least about 200.

4. Crystalline silicas according to claim 1, characterized in that they have an X-ray diffraction pattern presenting a doublet at the interplanar spacing d=3.65 Å.

5. Crystalline silicas according to claim 1, characterized in that they have an X-ray diffraction pattern presenting a doublet at the interplanar spacing d=3.05 to 3.06 Å and a singlet at the interplanar spacing d=2.98 to 3.00 Å.

* * * * *

UNITED STATES PATENT AND TRADEMARK OFFICE
CERTIFICATE OF CORRECTION

PATENT NO. : 4,781,906
DATED : November 1, 1988
INVENTOR(S) : Cahen, Raymond et al It is certified that error appears in the above—identified patent and that said Letters Patent is hereby corrected as shown below:

On the face of the patent:

column [73], Assignee: "Labofina, S.A., Brussels, Belgium"

should read

"Cosden Technology, Inc., Dallas, Texas"

Signed and Sealed this

Fourteenth Day of March, 1989

Attest:

DONALD J. QUIGG

Attesting Officer

Commissioner of Patents and Trademarks